United States Patent
Shibuya et al.

(10) Patent No.: US 7,771,656 B2
(45) Date of Patent: Aug. 10, 2010

(54) AUTOMATIC ANALYZER

(75) Inventors: Takeshi Shibuya, Hitachinaka (JP);
Hiroyasu Uchida, Hitachinaka (JP);
Katsuhiro Kambara, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 775 days.

(21) Appl. No.: 10/466,839

(22) PCT Filed: Jan. 23, 2001

(86) PCT No.: PCT/JP01/00141

§ 371 (c)(1),
(2), (4) Date: Jul. 22, 2003

(87) PCT Pub. No.: WO02/059624

PCT Pub. Date: Aug. 1, 2002

(65) Prior Publication Data

US 2004/0057872 A1    Mar. 25, 2004

(51) Int. Cl.
*G01N 21/00* (2006.01)
*G01N 31/00* (2006.01)
*G01N 15/06* (2006.01)

(52) U.S. Cl. .............. 422/64; 422/63; 422/65; 422/66

(58) Field of Classification Search ............ 422/63, 422/64, 65; 436/47; 435/287.3
See application file for complete search history.

(56) References Cited

U.S. PATENT DOCUMENTS

| 4,276,051 | A | * | 6/1981 | Ginsberg et al. | 436/47 |
| 4,678,752 | A | * | 7/1987 | Thorne et al. | 435/287.3 |
| 5,578,269 | A | * | 11/1996 | Yaremko et al. | 422/64 |
| 5,827,479 | A | | 10/1998 | Yamazaki et al. | |
| 2003/0026732 | A1 | * | 2/2003 | Gordon et al. | 422/63 |

* cited by examiner

*Primary Examiner*—Jill Warden
*Assistant Examiner*—Neil Turk
(74) *Attorney, Agent, or Firm*—Mattingly & Malur, P.C.

(57) ABSTRACT

A reagent dispensing mechanism (15), first and second dispensing-mechanism transfer means (26, 27), and a second reagent vessel (reagent cassette) carrying-in/out mechanism (24), which are constructed by employing an XY-mechanism, are arranged so as to travel above a reagent table (25) to carry in/out a reagent cassette (22). As compared with the case where the reagent cassette carrying-in/out mechanism (24) is installed radially of the reagent table (25), the area of an automatic analyzer in the horizontal direction can be reduced and a reagent vessel (16) can be moved to a predetermined position in a shorter time by combining the rotation of the reagent table (25) with the movement of the XY-mechanism. Further, as compared the case of dispensing reagents from reagent vessels in a matrix pattern by using the reagent dispensing/transferring mechanism, the travel distance of the transferring mechanism can be shortened and so can be the travel time. Thus, an analyzer adaptable as a machine of high processing capability with a shorter cycle time can be constructed.

5 Claims, 10 Drawing Sheets

AUTOMATIC ANALYZER

TECHNICAL FIELD

The present invention relates to an automatic analyzer suitable for agitating and mixing a sample with a reagent loaded on a reagent table, and then analyzing the sample.

BACKGROUND ART

An automatic analyzer is practiced as an apparatus for analyzing sera, urine, etc. of patients. Such an analyzer comprises a sample table including a sample vessel which contains a sample, such as a serum, a sampling mechanism for dispensing the sample, a reaction table including a reaction vessel in which the sample is mixed with a reagent to prepare a reaction solution and to develop a reaction, an agitating mechanism for agitating and mixing the reaction solution, a photometer for measuring the absorbance of the reaction solution, and a cleaning mechanism for cleaning the reaction vessel.

Further, the analyzer comprises two reagent tables on which a first reagent and a second reagent are loaded respectively as reagents to be added to the sample. Each of the reagent tables includes a driving mechanism for rotating the reagent table independently, and a reagent dispensing mechanism for sucking the reagent.

Recently, there has been an increasing demand for an analyzer capable of performing both biochemical analysis and immunity analysis by a single unit, which have been performed so far by separate dedicated analyzers. It is hence required to accurately perform a wide range of analysis covering from biochemical analysis to immunity analysis.

Accordingly, a demand for increasing the number of analysis items loadable on the automatic analyzer, i.e., the number of reagents, has also increased.

In view of such a demand, JP,A 9-72915 proposes a reagent storage in the form of a turntable for loading reagents thereon, in which reagent vessels are arranged along a plurality of circles in a concentric relation corresponding to the increasing number of reagents, and barcodes of the reagent thus arranged can be read.

In general, reagent vessels are employed such that sector-shaped reagent vessels are arranged on a reagent table in an annular form, or that rectangular reagent vessels are arranged in a matrix pattern. As a reagent dispensing mechanism, a rotating mechanism and an XY-mechanism are employed for the sector-shaped and rectangular reagent vessels, respectively, to perform dispensation of reagents and analysis of samples with high efficiency.

However, the number of reagents loadable on the reagent table is determined depending on the size of the reagent table itself. Therefore, if two reagent tables are arranged independently of each other and reagents are sucked and ejected from the reagent tables by using respective reagent dispensing mechanisms, the size of the reagent table is enlarged as the number of loadable reagents increases. As a result, the size of a body of the automatic analyzer is enlarged and so is the reagent dispensing mechanism.

Also, in the analyzer employing the rectangular reagent vessels arranged in a matrix pattern, the travel distance of the XY-mechanism becomes longer with an increase in the number of loadable reagents, and therefore the analyzer is not adaptable as a machine of high processing capability with a shorter cycle time.

Thus, even in the field of a multi-item analyzer requiring a large number of loadable reagents, it has been demanded to develop a small-sized analyzer having a high processing capability and high reliability.

To that end, JP,A 4-36658 discloses an automatic analyzer comprising a reagent storage in which a plurality of reagent vessels can be arranged in an annular form, reagent vessel carrying-in means for carrying the reagent vessel into the reagent storage in the radial direction of the reagent storage, and reagent vessel carrying-out means for carrying the reagent vessel out of the reagent storage in the radial direction of the reagent storage, wherein the reagent vessel can be carried out and in even during analysis of a sample.

With that construction, the number of loadable reagents can be increased without essentially enlarging the size of the reagent storage.

Additionally, other similar techniques regarding the automatic analyzer are disclosed in, e.g., JP,A 4-43962 and JP,A 4-50654.

DISCLOSURE OF THE INVENTION

With the technique disclosed in JP,A 4-36658, however, because the reagent vessel is carried in and out of the reagent storage in the radial direction of the reagent storage as described above, the reagent storage cannot be constructed of two parts, which are arranged in a concentric relation and are rotated independently of each other. Hence, there is a limit in increasing the number of times at which the reagent storage is carried in and out. In order to be adapted for an increase in the number of loadable reagents beyond such a limit, a problem arises in that the analyzer size must be enlarged.

Also, because the reagent vessel is carried in and out of the reagent storage in the radial direction of the reagent storage, the carrying-in means and the carrying-out means require to be provided separately from each other and an area for installing those means is required. This raises a problem that it is difficult to reduce the analyzer size and the disclosed technique is not suitable for a machine of high processing capability.

An object of the present invention is to inexpensively realize an automatic analyzer, which can suppress the analyzer size from increasing with an increase in the number of loadable reagents and which is adaptable for a high processing capability.

According to the present invention, an automatic analyzer with high reliability can be realized because reagent management, including carrying of reagents, can be automated.

Further, according to the present invention, an automatic analyzer can be realized which is flexibly adaptable for even an analysis item having a complicated reaction sequence.

To achieve the above object, the present invention is constituted as follows:

(1) An automatic analyzer comprising a reagent table on which a plurality of reagent vessels are loadable, and a reagent dispensing mechanism capable of sucking a reagent from the reagent vessels and ejecting the reagent to a reaction vessel, the automatic analyzer further comprising reagent-dispensing-mechanism transfer means for moving the reagent dispensing mechanism from a particular reagent sucking position to a reagent ejecting position, in which the reagent is ejected to the reaction vessel, through a space above the reagent table, reagent vessel carrying-in/out means for performing carrying-in of the reagent vessel from a reagent vessel movement standby position to a reagent vessel loading position and carrying-out of the reagent vessel from the reagent vessel loading position to a reagent vessel unloading position through a space above the reagent table, and control means for controlling operations of the reagent table, the reagent dispensing mechanism, the reagent-dispensing-mechanism transfer means, and the reagent vessel carrying-in/out means, wherein the reagent table includes a plurality of annular reagent vessel holders arranged in a concentric relation, the plurality of annular reagent vessel holders being driven for rotation independently of each other.

(2) In the above (1), preferably, the automatic analyzer further comprises reagent vessel carrying means for carrying the reagent vessel placed in a particular position to the reagent vessel movement standby position, reading means for reading specific information of the reagent, which is indicated on the reagent vessel carried by the reagent vessel carrying means, and an information storage section for storing the specific information of the reagent read by the reading means, wherein the control means instructs the carrying-in of the reagent vessel from the reagent vessel movement standby position to the reagent vessel loading position in accordance with the specific information of the reagent.

(3) In the above (1), preferably, the control means includes determining means for determining whether the reagent vessel on the reagent table is to be carried out of the reagent table, and if it is determined that the reagent vessel is to be carried out based on the expiration date of the reagent or the amount of remaining reagent calculated from the specific information of the reagent stored in the information storage section, the control means carries the reagent vessel on the reagent table from the reagent vessel loading position to the reagent vessel unloading position by using the reagent vessel carrying-in/out means.

(4) In the above (1) or (2), preferably, the automatic analyzer further comprises display means for displaying movement information of the reagent vessel when the reagent vessel is loaded onto or unloaded from the reagent table.

(5) In the above (1), preferably, the control means controls the operation of loading the reagent vessel onto the reagent table such that the reagent vessel is loaded in a vacant area in one of the annular reagent vessel holders on the inner peripheral side with priority over a vacant area in another holder on the outer peripheral side.

(6) In the above (1), preferably, the automatic analyzer further comprises an annular reaction table on which the reaction vessels are placed, wherein the reaction table is rotated under control of the control means, and two or more reagent dispensing mechanism are controlled such that reagents to be added at different timings are added to the reaction vessels during the same period in a rotation cycle in which the reaction table is stopped.

Consequently, by combining the reagent table, on which the reagent vessels are arranged in an annular form, with the reagent dispensing mechanism employing an XY-mechanism, it is possible to inexpensively realize an automatic analyzer, which can suppress the analyzer size from increasing and which is adaptable for a high processing capability.

Also, an automatic analyzer with high reliability can be realized because reagent management, including carrying of reagents, can be automated.

Further, an automatic analyzer can be realized which is flexibly adaptable for even an analysis item having a complicated reaction sequence.

BEST MODE FOR CARRYING OUT THE INVENTION

An embodiment of the present invention will be described below with reference to the drawings.

Figure 1:
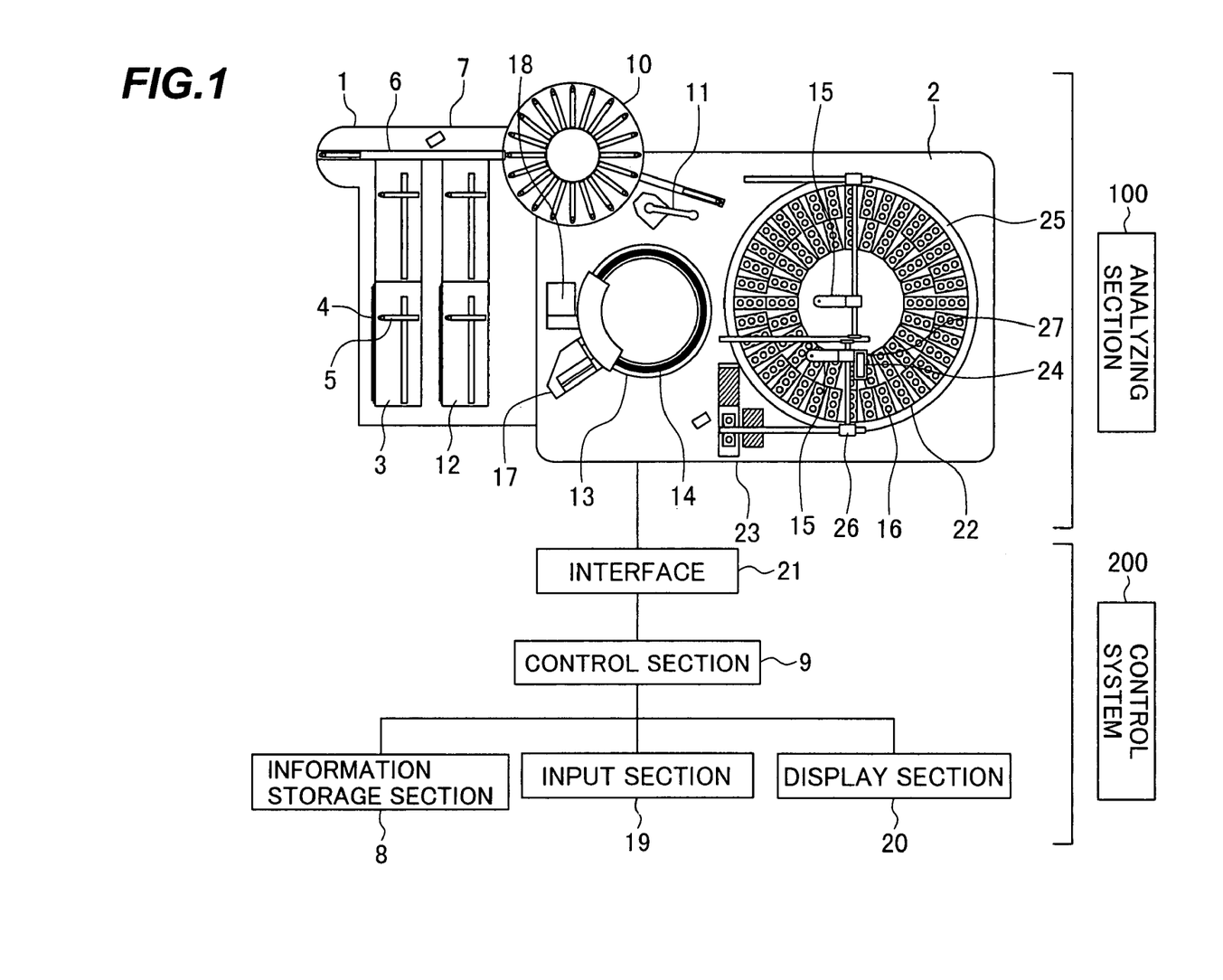
FIG. 1 is a schematic view showing the construction of one embodiment of an automatic analyzer to which the present invention is applied.

FIG. 1 is a schematic view showing the construction of one embodiment of an automatic analyzer to which the present invention is applied. This embodiment represents an automatic analyzer comprising two units, i.e., a rack sampler 1 and an analyzing section 2 (100).

In a rack supply section 3 of the rack sampler 1, a sample vessel 4 containing a sample is loaded while it is set in a rack 5. When analysis of the sample is started, each rack 5 is successively carried toward the analyzing section 2 via a rack supply line 6.

During the carrying of the sample vessel 4 toward the analyzing section 2 via the rack supply line 6, the sample ID or the rack ID put on the sample vessel 4 is read by a barcode reader 7. Then, a control section 9 executes collation of the sample with requested analysis items and stores analysis information regarding the sample in an information storage section 8.

Under control of the control section 9, the rack 5 is held on a rack rotating table 10 and thereafter carried to a sampling mechanism 11, and the sample is analyzed based on the analysis information previously stored in the information storage section 8. Subsequently, the rack 5, for which the analysis has finished, is returned again to the rack rotating table 10 and then stowed in a rack stowing section 12 via the rack supply line 6.

The analysis of the sample is performed as follows. The sampling mechanism 11 dispenses the sample contained in the sample vessel 4 to a reaction vessel 14, which is disposed in an annular form on a reaction table 13. Then, a reagent contained in a reagent vessel 16, which is arranged on a reagent table 25, is adds to the sample, as required, by a reagent dispensing mechanism 15. Thereafter, the sample and the reagent are agitated and mixed by an agitating mechanism (not shown), and the absorbance of a mixed solution is measured using a photometer 17.

The reaction vessel 14, for which the measurement has finished, is cleaned after the end of each measurement by a cleaning mechanism 18 to be ready for a next cycle of the measurement.

A control system 200 comprises the control section 9, the information storage section 8 for storing various kinds of information regarding the analysis, an input section 19 for inputting information, and a display section 20 for displaying information. The control system 200 controls the analysis process and the mechanism operation in the analyzing section 100 via an interface 21.

In addition to two reagent dispensing mechanisms 15, the analyzer shown in FIG. 1 further includes a first reagent vessel carrying mechanism 23 for carrying a reagent cassette 22, in which a plurality of reagent vessels 16 are loadable, into the analyzing section 2 and for reading the specific information of the reagent, a second reagent vessel carrying-in/out mechanism 24 associated with the reagent dispensing mechanism 15 and lifting up the reagent cassette while fixedly holding it, a reagent table 25 on which the reagent cassettes 22 can be loaded in an annular form, and first and second reagent-dispensing-mechanism transfer means 26, 27 capable of adding the reagent from the reagent vessel 16 to the reaction vessel 14 and capable of carrying the reagent cassette 22 to the reagent table 25 from the first reagent vessel carrying mechanism 23.

The operation of the automatic analyzer according to one embodiment of the present invention will be described below in detail.

A description is first made of a manner of loading the reagent cassette 22.

Figure 2:
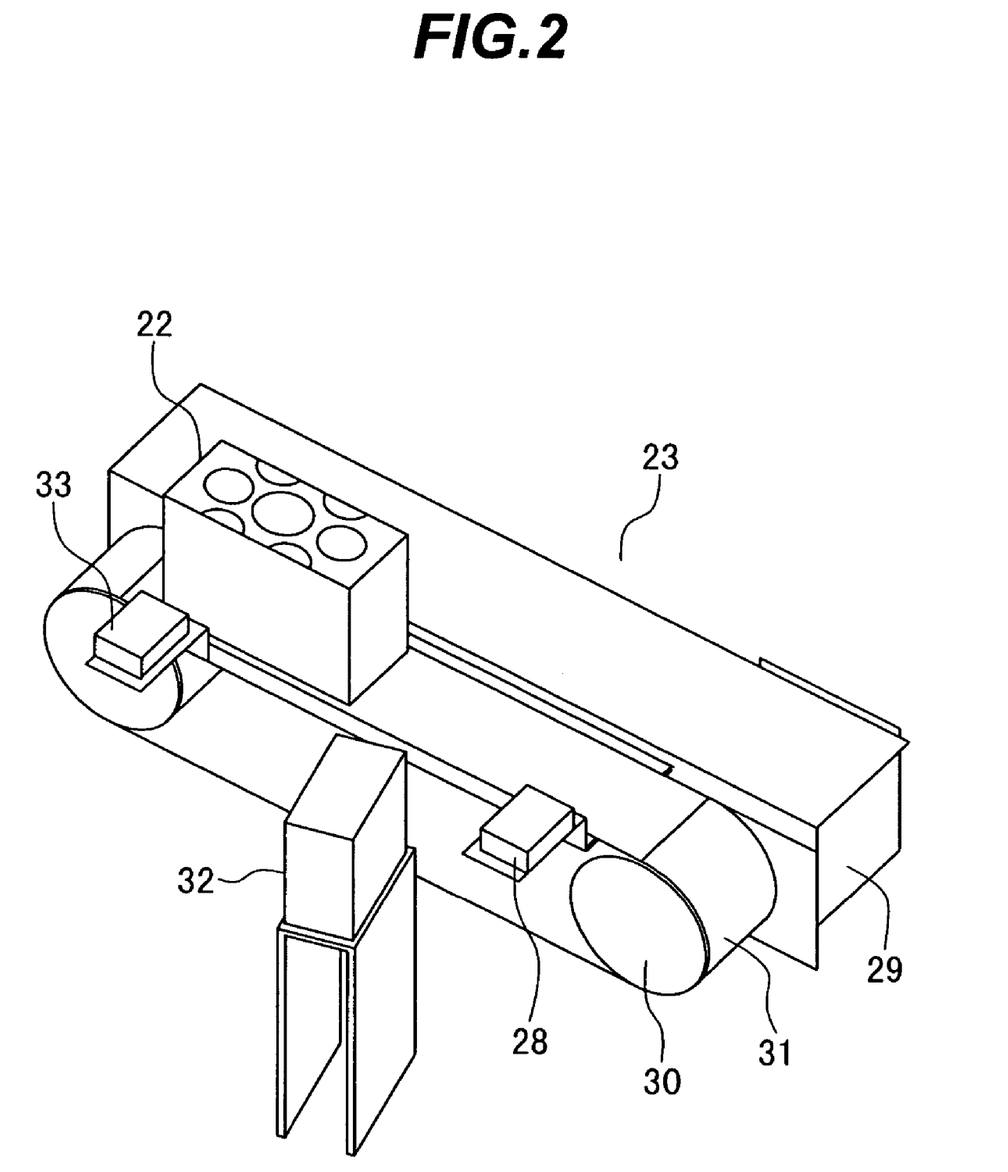
FIG. 2 is a detailed view of a first reagent vessel carrying mechanism shown in FIG. 1.
Figure 3:
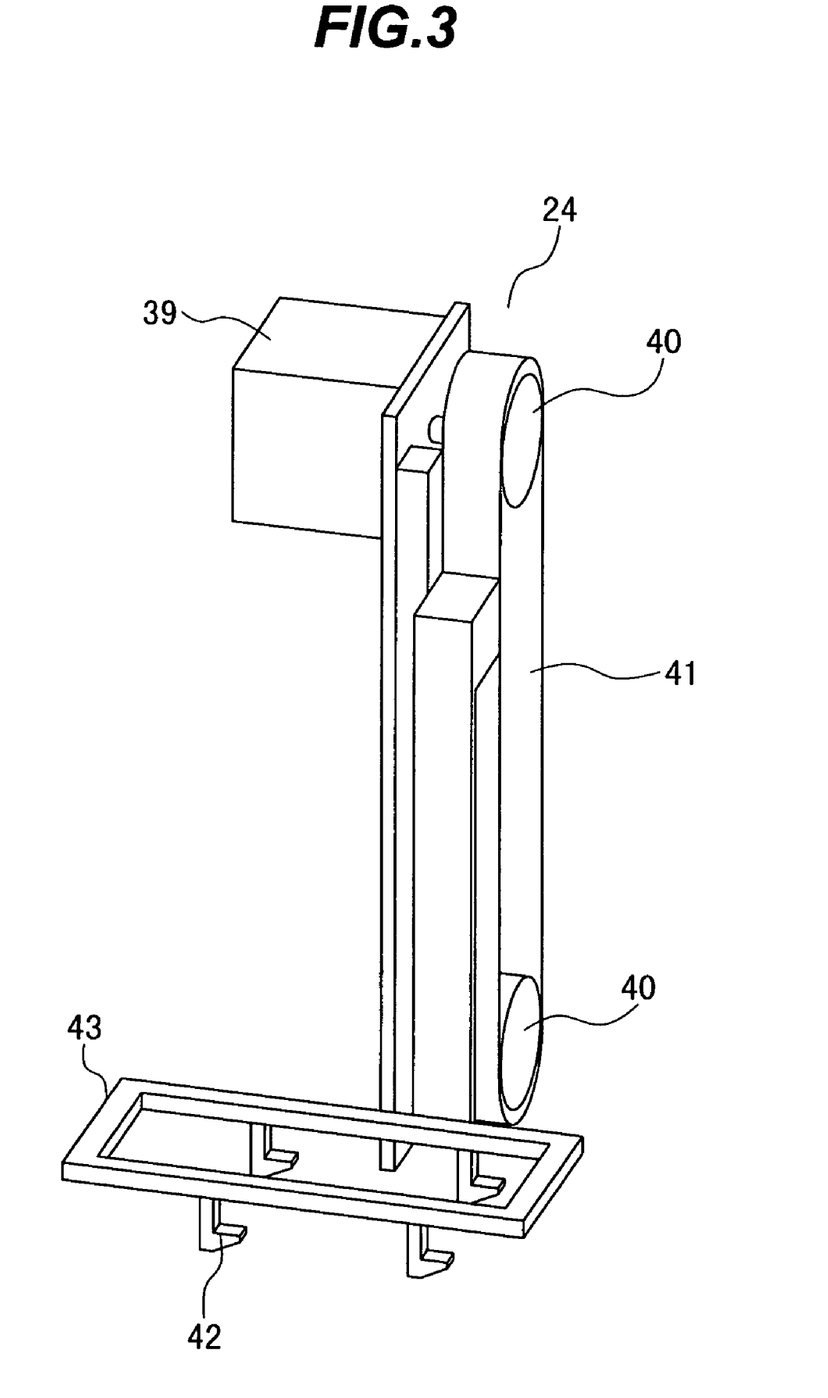
FIG. 3 is a detailed view of a second reagent vessel carrying mechanism shown in FIG. 1.
Figure 4:
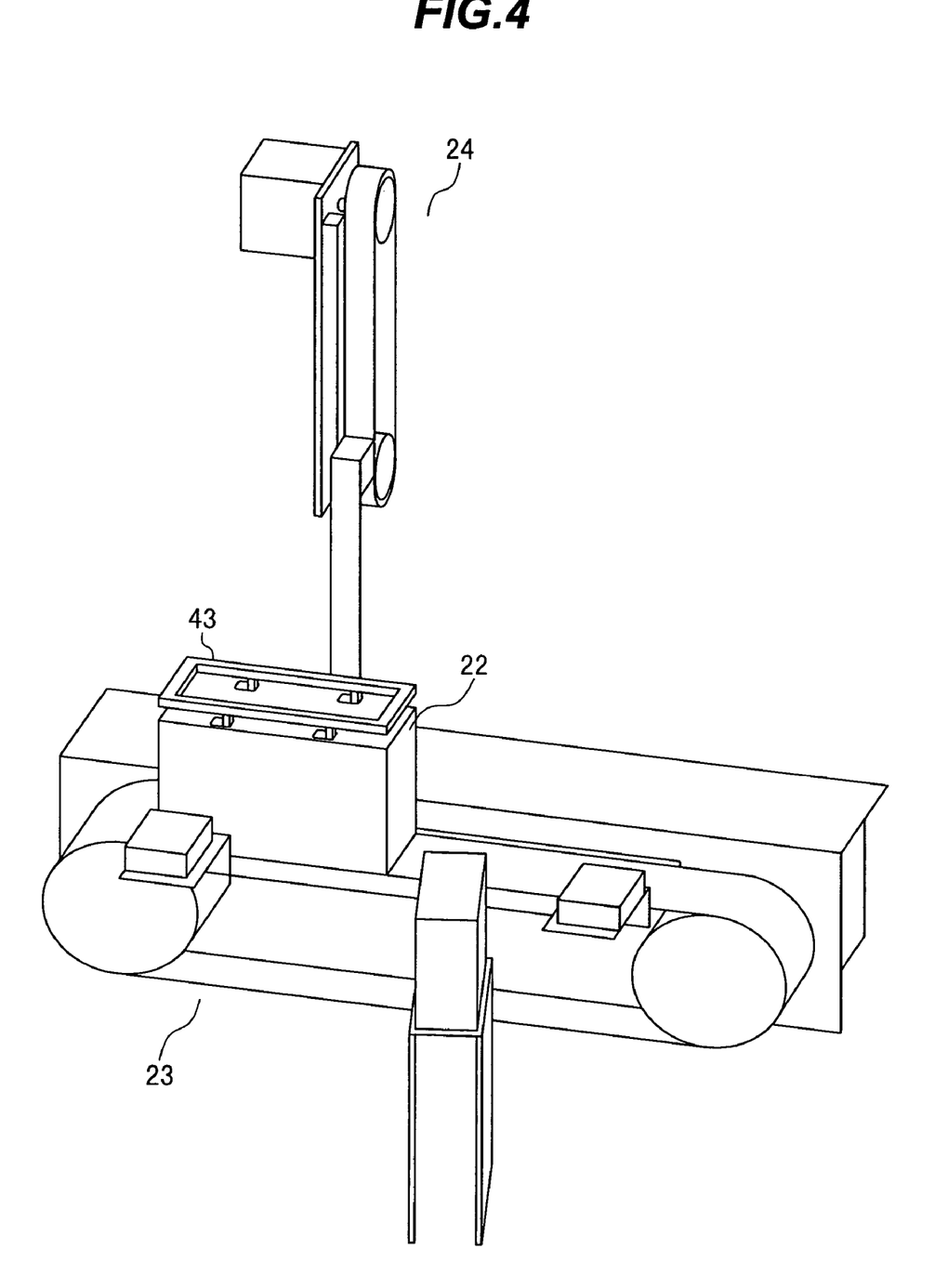
FIG. 4 is a view for explaining the operation of the second reagent vessel carrying mechanism shown in FIG. 1.
Figure 5:
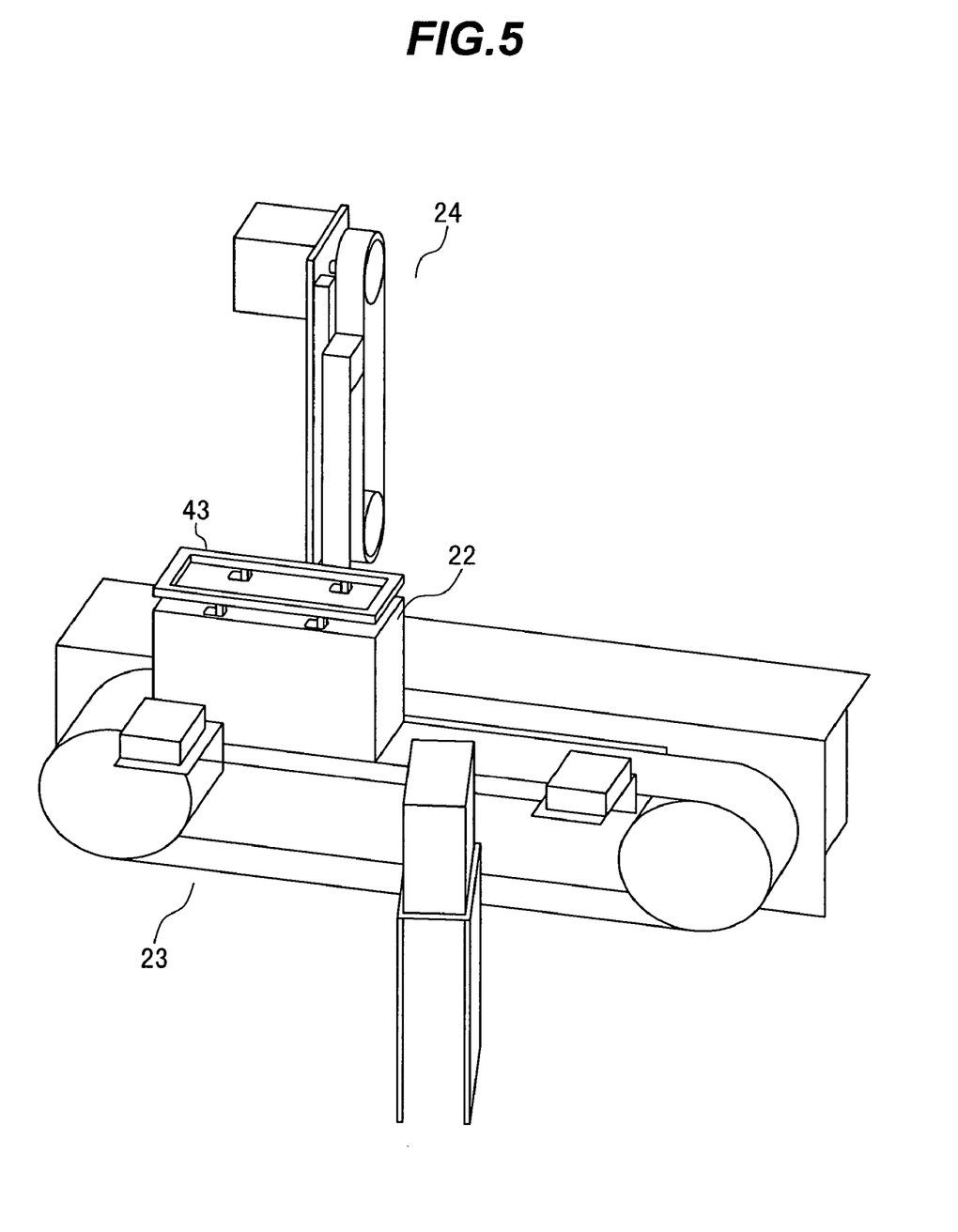
FIG. 5 is a view for explaining the operation of the second reagent vessel carrying mechanism shown in FIG. 1.
Figure 6:
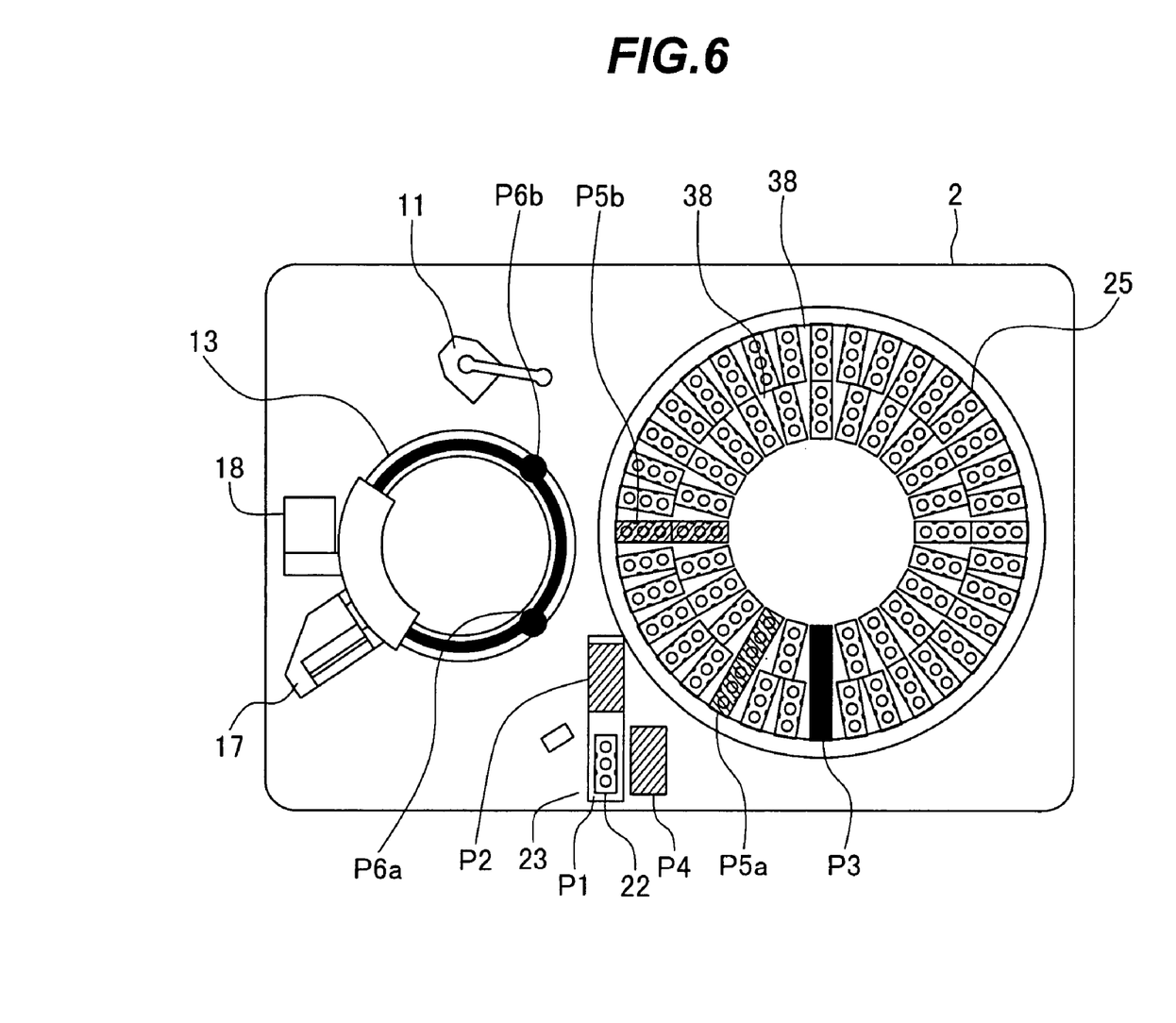
FIG. 6 is a view for explaining reagent cassette loading/unloading positions and reagent sucking positions of the automatic analyzer to which the present invention is applied.
Figure 7:
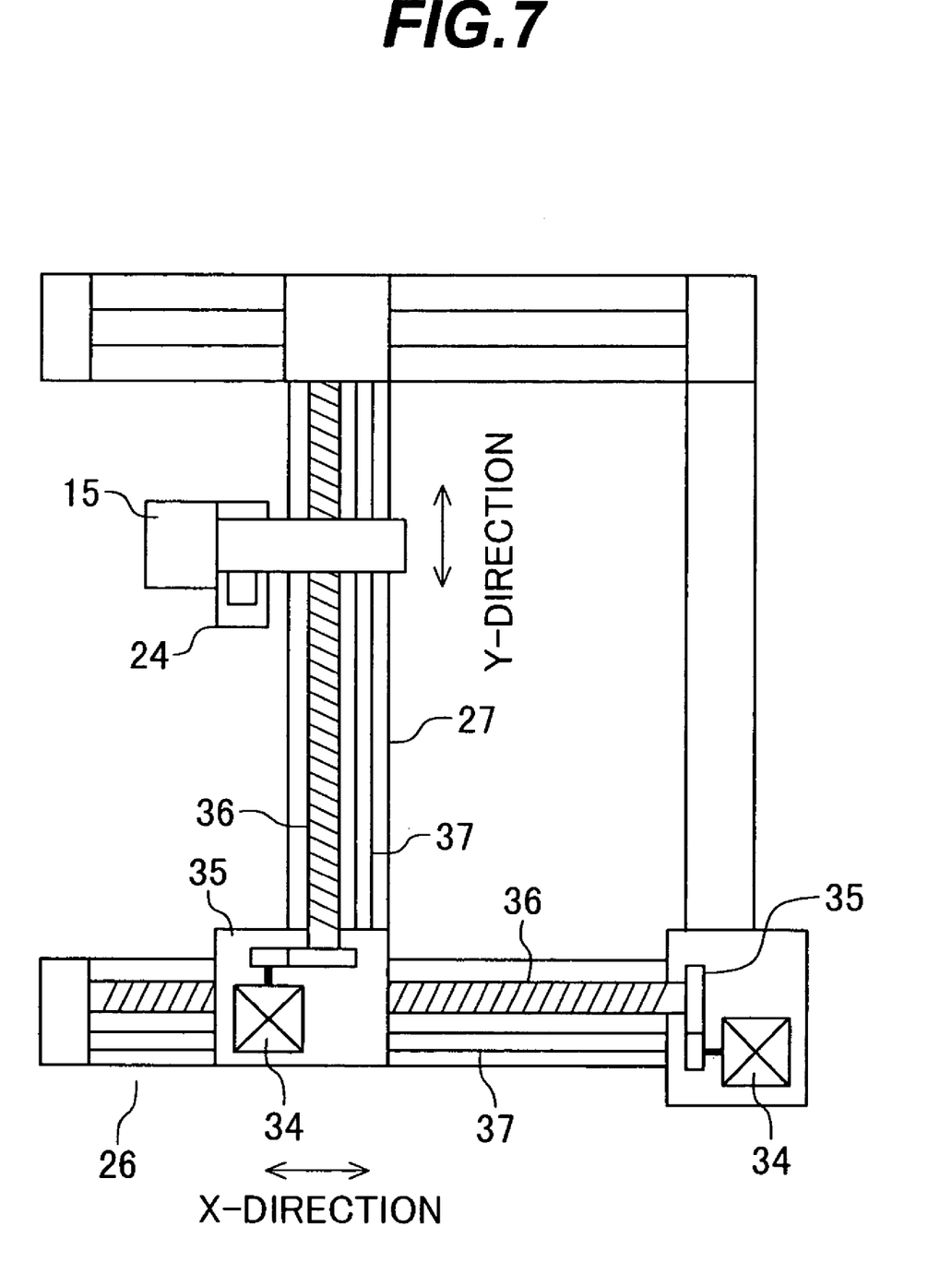
FIG. 7 is a plan view of first and second reagent dispensing/transferring mechanisms shown in FIG. 1.

FIG. 2 is a detailed view of the first reagent vessel carrying mechanism 23, and FIG. 3 is a detailed view of the second reagent vessel carrying mechanism 24. Also, FIGS. 4 and 5 are each a view for explaining the operation of the second reagent vessel carrying-in/out mechanism 24. Further, FIG. 6 is a schematic view showing loading and unloading positions of the reagent cassette 22. FIG. 7 is a schematic view showing the construction of first and second reagent-dispensing-mechanism transfer means 26, 27 dispensing the first reagent, and FIG. 8 is a flowchart of the operation for loading the reagent cassette 22.

Figure 8:
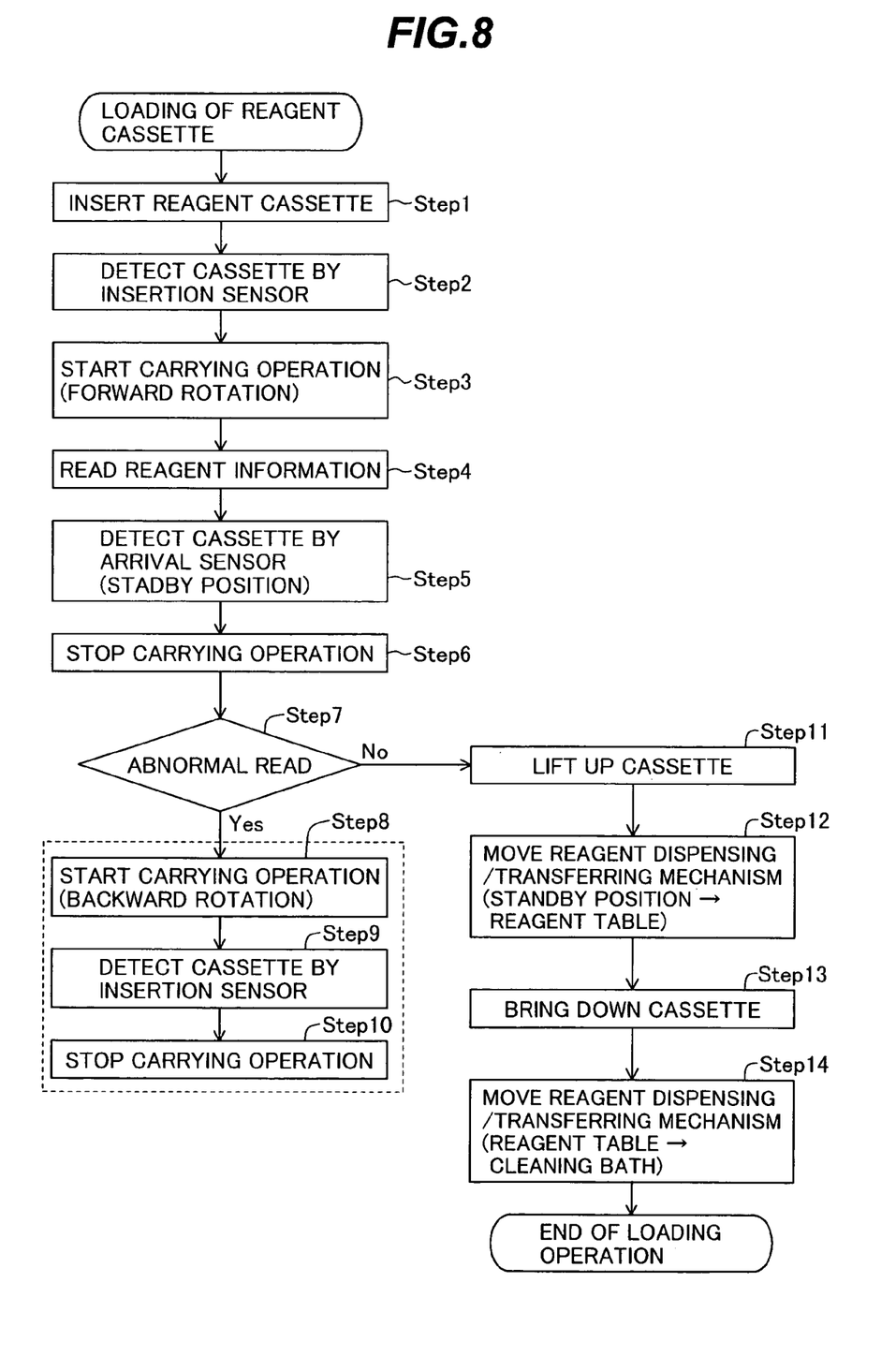
FIG. 8 is a flowchart of the reagent cassette loading operation in the embodiment of the present invention.

Referring to FIG. 8, when newly loading the reagent cassette 22 on the reagent table 25, the reagent cassette 22 is inserted in a reagent cassette inserting position P1 (FIG. 6) (Step 1). When the insertion of the reagent cassette 22 is detected by an insertion sensor 28 (FIG. 2) (Step 2), a motor 29 starts rotation and the rotation is transmitted to a belt 31 through a pulley 30, whereupon the carrying of the reagent cassette 22 into the analyzer is started (Step 3).

During the carrying of the reagent cassette 22, the specific information of the reagent is read by a barcode reader 32 (Step 4) and then stored in the information storage section 8. When the reagent cassette 22 is carried to a reagent vessel movement standby position P2 (FIG. 6), an arrival sensor 33 detects the reagent cassette 22 (Step 5), whereupon the rotation of the motor 29 is stopped and the carrying of the reagent cassette 22 is stopped (Step 6).

If it is here determined that the previously read specific information of the reagent is improper and false read has occurred (Step 7), the motor 29 is rotated in the direction opposed to that in the above case (Step 8) for carrying the reagent cassette 22 back to the reagent cassette inserting position P1. After the insertion sensor 28 detects the reagent cassette 22 (Step 9), the carrying operation is stopped (Step 10).

Thus, the reagent can be taken out for reconfirmation.

If there is no abnormality in the read specific information of the reagent (Step 7), the reagent cassette 22 is lifted up from the reagent vessel movement standby position P2 by the second reagent vessel carrying-in/out mechanism 24 (Step 11), which is associated with the reagent dispensing mechanisms 15 and is capable of lifting up the reagent cassette 22 while fixedly holding it.

The construction and operation of the second reagent vessel carrying-in/out mechanism 24 will now be described with reference to FIGS. 3, 4 and 5.

The second reagent vessel carrying-in/out mechanism 24 includes a motor 39. The motor 39 and two pulleys 40, 40 move a belt 41 so as to reciprocate between the two pulleys 40. The reciprocating direction of the belt 41 is set to be substantially the same as the direction of a rotary shaft of the reagent table 25.

Further, a reagent cassette lifting-up member 43 is attached to the belt 41. With the movement of the belt 41, the reagent cassette lifting-up member 43 is also movable substantially in the same the direction as that of the rotary shaft of the reagent table 25.

In addition, the reagent cassette lifting-up member 43 is provided with hooks 42 for lifting up the reagent cassette 22. The reagent cassette lifted up by the hooks 42 is movable in the up-and-down direction with respect to the automatic analyzer.

On the other hand, the reagent cassette 22 has holes used for lifting up it, which are formed in positions corresponding to the hooks 42. By inserting and engaging the hooks 42 in the holes of the reagent cassette 22, the reagent cassette 22 can be lifted up to a level at which it is movable in a horizontal plane (FIGS. 4 and 5).

Then, the reagent cassette 22 is moved from the reagent vessel movement standby position P2 to a reagent vessel loading position P3, or from the reagent vessel loading position P3 to a reagent vessel unloading position P4.

Furthermore, as shown in FIG. 7, the reagent dispensing mechanisms 15, to which the second reagent vessel carrying-in/out mechanism 24 is attached, is movable in a horizontal plane of the automatic analyzer by the first and second reagent-dispensing-mechanism transfer means 26, 27.

The first reagent-dispensing-mechanism transfer means 26 includes a moving mechanism comprising, e.g., a ball screw 36 and a guide 37, and it can move the second reagent-dispensing-mechanism transfer means 27, which is fixed to the moving mechanism, to the right-and-left direction (X-direction) as viewed on the drawing through a transmission mechanism 35 with driving of a motor 34.

Similarly, the second reagent-dispensing-mechanism transfer means 27 includes a moving mechanism comprising, e.g., a ball screw 36 and a guide 37, and it can move the reagent dispensing mechanism 15, which is fixed to the moving mechanism, to the up-and-down direction (Y-direction) as viewed on the drawing through a transmission mechanism 35 with driving of a motor 34.

With that construction, the reagent dispensing mechanism 15 and the second reagent vessel carrying-in/out mechanism 24 associated therewith are able to move in the horizontal plane.

As described above, the reagent cassette 22 is carried from the reagent vessel movement standby position P2 to the reagent vessel loading position P3 on the reagent table 25 while the reagent cassette 22 is held in a hanged state (Step 12).

In an example of the construction shown in the drawing, the reagent table 25 has annular reagent vessel holders 38, which are arranged in a dual pattern and each of which has a single loading position. Note that the number of annular reagent vessel holders 38 constituting the reagent table 25 may be one or three, and at least one reagent vessel loading position P3 is required for each of the annular reagent vessel holders 38.

When there are two or more annular reagent vessel holders 38, these holders are controlled so as to rotate independently of each other.

The reagent cassette 22 is brought down in the reagent vessel loading position P3 (Step 13). After the bringing-down operation, the reagent dispensing mechanism 15 is moved to the position of a not-shown cleaning bath which is usually on standby (Step 14). If there is a vacant area in one of the annular reagent vessel holders 38 on the inner peripheral side, the operation of loading the reagent cassette 22 or the reagent vessel 16 onto the reagent table 25 is controlled such that the reagent cassette 22 or the reagent vessel 16 is loaded in the vacant area in the inner peripheral side holder 38 with priority over a vacant area in the outer peripheral side holder 38.

Stated another way, for the purpose of preventing an excessive unbalance in arrangement of the reagent cassettes 22 on the reagent table 25, the control section 9 desirably controls the loading operation of the reagent cassette 22 onto the reagent table 25 such that the reagent cassette 22 is loaded in the vacant area on the inner peripheral side closer to the center of rotation of the reagent table 25 with priority over the vacant area on the outer peripheral side.

When the reagent cassette 22 is loaded, information regarding the cassette movement is displayed on the display section 20, such as a monitor or a printer, so that an analyzer user can confirm the displayed information.

A manner of unloading the reagent cassette 22 will be described below.

Figure 9:
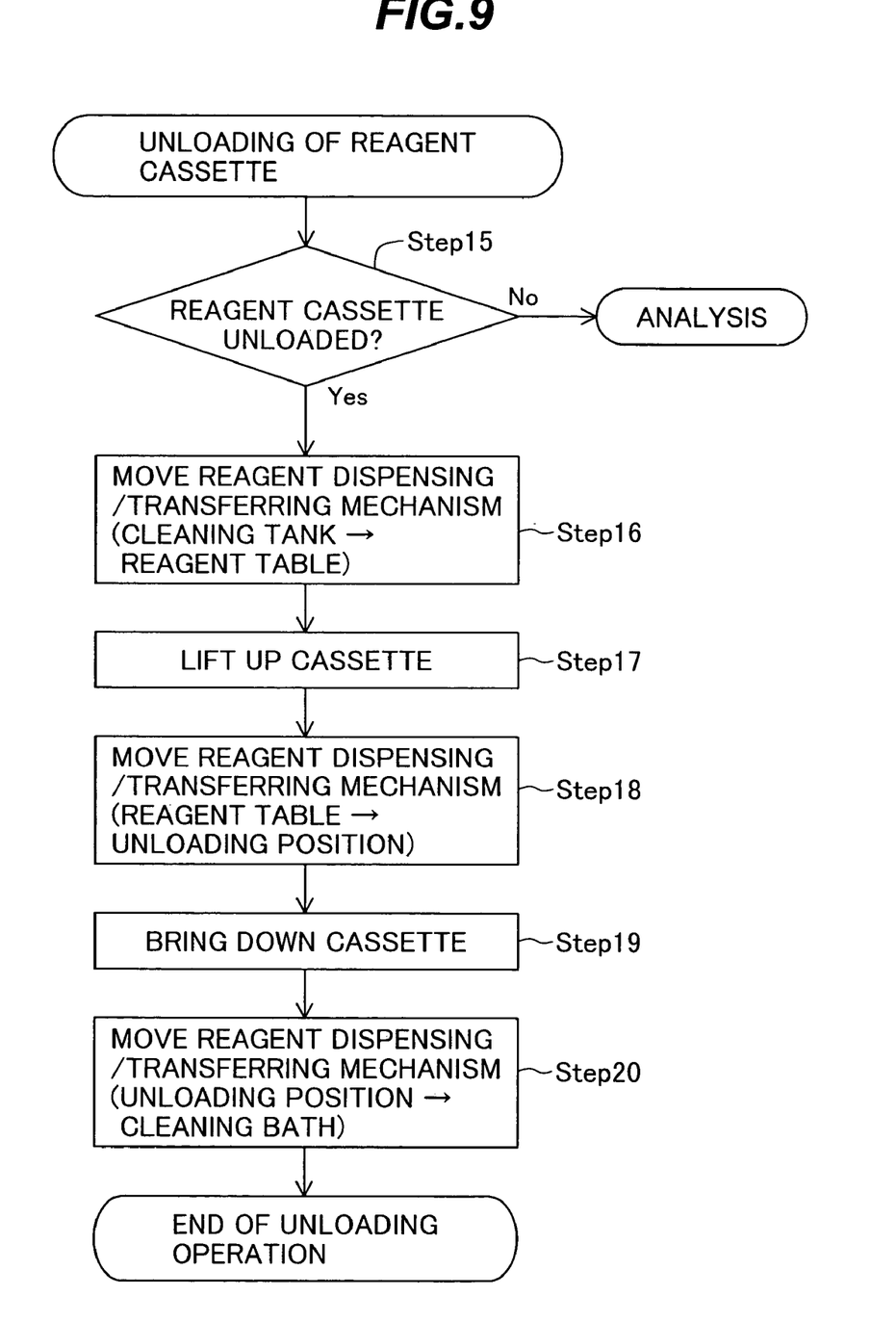
FIG. 9 is a flowchart of the reagent cassette unloading operation in the embodiment of the present invention.

FIG. 9 is a flowchart of the operation of unloading the reagent cassette 22.

Referring to FIG. 9, when reagent cassette unloading instruction is entered from the external input section, such as a keyboard, or when the amount of remaining reagent calculated from the specific information of the reagent exceeds a preset value, or when the reagent is over the expiration date, the control section 9 determines that the reagent cassette 22 is to be unloaded from the reagent table 25 (Step 15).

The control section 9 rotates the reagent table 25 to such an extent that the relevant reagent cassette 22 is moved to the reagent vessel loading position P3 described above, and at the same time moves the second reagent vessel carrying-in/out mechanism 24 to the reagent vessel loading position P3 (Step 16). The reagent cassette 22 is lifted up from the reagent vessel loading position P3 (Step 17) and then moved to the reagent vessel unloading position P4 (Step 18). Thereafter, the reagent cassette 22 is brought down in the reagent vessel unloading position P4 (Step 19).

Subsequently, the second reagent vessel carrying-in/out mechanism 24 is moved to the position of the cleaning bath not shown (Step 20). When the reagent cassette 22 is unloaded, information regarding the cassette movement is displayed on the display section 20, such as a monitor or a printer, so that the analyzer user can confirm the displayed information.

The reagent vessel movement standby position P2 may serve also as the reagent vessel unloading position P4. The reagent cassette 22 can be carried to the reagent vessel inserting position P1 by utilizing the first reagent vessel carrying mechanism 23, and can be automatically unloaded by externally providing a container for receiving the unloaded reagent cassettes.

With the operation described above, it is possible to automate the analyzer from the stage of carrying the reagent into the analyzer and to constitute an automatic analyzer with higher reliability.

Figure 10:
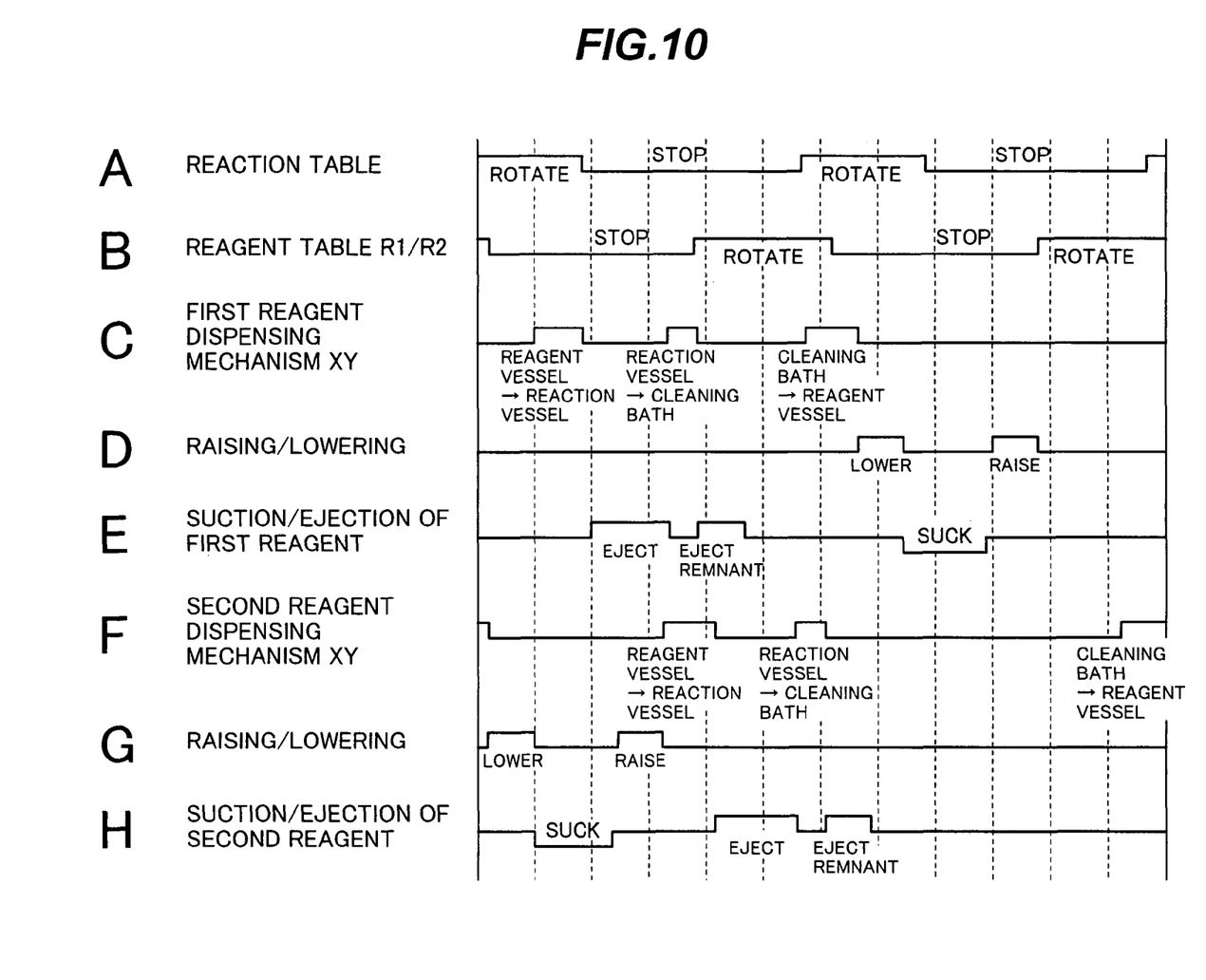
FIG. 10 is a time chart in the embodiment of the present invention.

FIG. 10 is a time chart in the case where one embodiment of the present invention is applied to an automatic analyzer with a processing capability of 600 tests/hour.

FIG. 10 represents an example in which a single driving mechanism controls the two annular reagent vessel holders 38 on the inner and outer peripheral sides, and the reagent cassettes 22 each containing a first reagent or a second reagent are loaded on the reagent table 25 without being allocated with regard to areas.

First, after dispensing the sample into the reaction vessel 14 by using the sampling mechanism 11, the reaction table 13 is rotated to a first reagent ejecting position P6a (FIG. 6)((A) in FIG. 10). To dispense the first agent, the reagent table 25 is rotated to a first reagent sucking position P5a ((B) in FIG. 10). The first reagent dispensing mechanism 15 is moved to the first reagent sucking position P5a by using the first and second reagent-dispensing-mechanism transfer means 26, 27, then the reagent is sucked from the reagent vessel 16, and the reagent is ejected in the first reagent ejecting position P6a to which the reaction vessel 14 has moved ((C), (D) and (E) in FIG. 10).

Subsequently, to dispense the second reagent at the timing at which the second reagent is to be dispensed, the reagent table 25 is rotated to a second reagent sucking position P5b. The second reagent dispensing mechanism 15 is moved to the second reagent sucking position P5b by using the first and second reagent-dispensing-mechanism transfer means 26, 27, then the reagent is sucked from the reagent vessel 16, and the reagent is ejected into the reaction vessel 14 which has moved to the second reagent ejecting position P6a ((F), (G,) and (H) in FIG. 10).

A series of the above-described operations are executed in a cyclic manner, and therefore can be represented by the time chart shown in FIG. 10. In this embodiment, the reaction table 25 stops the operation twice during each rotation cycle of 6 seconds. The sample and the reagents are added in one stopped state, while they are agitated and mixed in the other stopped state. In other words, at the reagent adding timing corresponding to the one stopped state, the first reagent and the second reagent are both added to the reaction vessels 14.

In order to realize such a series of the operations, the operation of rotating and stopping the reagent table 25 is repeated twice during each cycle of 6 seconds. One half cycle is utilized for sucking the first reagent and the other half cycle is utilized for sucking the second reagent. Thus, the first reagent and the second reagent are sucked in the respective reagent sucking positions P5, and are both ejected to the reaction vessels 14 in the same stopped state during each rotation cycle of the reaction table 13.

As described above, combining the reagent table 25, on which the reagent vessels 16 are arranged in an annular form, with the reagent dispensing mechanism 15, the first and second dispensing-mechanism transfer means 26, 27, and the second reagent vessel carrying-in/out mechanism 24, which are constructed by employing the XY-mechanism, makes it possible to always suck the reagent in a predetermined position and to always carry in/out the reagent vessel 16 in a predetermined position.

Stated another way, the reagent dispensing mechanism 15, etc. employing the XY-mechanism are constructed so as to travel above the reagent table 25 to carry in/out the reagent cassette 22. As compared with the prior art where the reagent cassette carrying-in/out means is installed radially of the reagent table, therefore, the area of the automatic analyzer in the horizontal direction can be reduced and the reagent vessel can be moved to a predetermined position in a shorter time by combining the rotation of the reagent table 25 with the movement of the XY-mechanism. Further, as compared the prior art of dispensing reagents from reagent vessels in a matrix pattern by using the reagent dispensing/transferring mechanism, the travel distance of the transferring mechanism can be shortened and so can be the travel time. Thus, an analyzer adaptable as a machine of high processing capability with a shorter cycle time can be constructed.

As a consequence, an automatic analyzer capable of suppressing the analyzer size from increasing with an increase in the number of loadable reagents and being adaptable for a high processing capability can be inexpensively realized.

Further, since a position in which the reagent is to be added to the reaction vessel 14 can be relatively freely set, the automatic analyzer is flexibly adaptable for even an analysis item having a complicated reaction sequence.

INDUSTRIAL APPLICABILITY

According to the present invention, the dispensation of the reagent and the carrying-in/out of the reagent cassette to and from the reagent table are performed by combining the reagent table, on which the reagent vessels are arranged in an annular form, with the reagent dispensing mechanism employing the XY-mechanism. With that construction, it is possible to inexpensively realize an automatic analyzer, which can suppress the analyzer size from increasing with an increase in the number of reagent vessels and reagent cassettes used and which is adaptable for a high processing capability.

Also, an automatic analyzer with high reliability can be realized because reagent management, including carrying of reagents, can be automated.

Further, an automatic analyzer can be realized which is flexibly adaptable for even an analysis item having a complicated reaction sequence.

The invention claimed is:

1. An automatic analyzer comprising:
a rotatable reagent table on which a plurality of reagent vessels, each holding a reagent, are held, said reagent table including a plurality of annular reagent vessel holders holding said reagent vessels;
an annular reaction table positioned adjacent said rotatable reagent table and holding a plurality of reaction vessels;
a first reagent vessel carrying-in/out mechanism for lifting up one of said reagent vessels positioned at a reagent vessel movement standby position adjacent said one reagent table and for lowering said reagent vessel to a reagent vessel loading position;
a reagent dispensing mechanism for sucking a reagent in from said one reagent vessel and for ejecting the reagent to one of said reaction vessels, said reagent dispensing mechanism being directly mechanically connected to said first reagent vessel carrying-in/out mechanism;
first and second transfer means directly mechanically connected to each other for moving said reagent dispensing mechanism and said first reagent carrying-in/out mechanism in X and Y directions in a horizontal plane through a space above said reagent table;
a control system for controlling operations of said rotatable reagent table, said reagent dispensing mechanism, said first and second transfer means and said first reagent vessel carrying-in/out mechanism; and
a photometer for measuring an absorbance of a solution of a reagent and a sample mixed in said one reaction vessel.

2. The automatic analyzer according to claim 1 further comprising,
a second reagent vessel carrying-in/out mechanism for carrying a reagent vessel placed in a particular position to the reagent vessel movement standby position;
a bar code reader for reading specific information of a reagent indicated on the reagent vessel carried by said second reagent vessel carrying mechanism; and
an information storage section for storing the specific information of the reagent read by said bar code reader;
wherein said control system instructs the carrying-in of the reagent vessel from the reagent vessel movement standby position to the reagent vessel loading position and to said first reagent vessel carrying-in/out mechanism and said first and second transfer means in accordance with the specific information of the reagent.

3. An automatic analyzer according to claim 1, further comprising a display section for displaying movement information of a reagent vessel when the reagent vessel is loaded onto or unloaded from said rotatable reagent table.

4. The automatic analyzer according to claim 1, wherein said annular reagent vessel holders include an inner peripheral side annular reagent vessel holder and a second, separate outer peripheral side annular reagent vessel holder positioned outside of and surrounding said inner peripheral side annular reagent vessel holder, and wherein said control system controls the operation of loading a reagent vessel onto said reagent table such that a reagent vessel is loaded into a vacant area in one of said annular reagent vessel holders on the inner peripheral side annular reagent vessel holder with a priority over a vacant area in said outer peripheral side annular reagent vessel holder.

5. The automatic analyzer according to claim 1, further comprising another reagent dispensing mechanism and wherein said annular reaction table is rotated under control of said control system, and both reagent dispensing mechanisms are controlled such that reagents to be added at different times are added to a reaction vessel during the same period in a rotation cycle in which said annular reaction table is stopped.

* * * * *

UNITED STATES PATENT AND TRADEMARK OFFICE
CERTIFICATE OF CORRECTION

PATENT NO. : 7,771,656 B2 Page 1 of 1
APPLICATION NO. : 10/466839
DATED : August 10, 2010
INVENTOR(S) : T. Shibuya et al.

It is certified that error appears in the above-identified patent and that said Letters Patent is hereby corrected as shown below:

ON THE TITLE PAGE

Item (86) PCT No. should read as follows:

(86)   PCT No:         ~~PCT/JP01/00141~~ PCT/JP01/00414

Signed and Sealed this

Nineteenth Day of October, 2010

David J. Kappos
*Director of the United States Patent and Trademark Office*